(12) United States Patent
Levy

(10) Patent No.: US 10,575,713 B2
(45) Date of Patent: Mar. 3, 2020

(54) RIGID MEDICAL SURGERY ILLUMINATING DEVICE

(71) Applicant: 270 SURGICAL LTD., Netanya (IL)

(72) Inventor: Avraham Levy, Kfar Shmaryahu (IL)

(73) Assignee: 270 SURGICAL LTD., Netanya (IL)

( * ) Notice: Subject to any disclaimer, the term of this patent is extended or adjusted under 35 U.S.C. 154(b) by 0 days.

(21) Appl. No.: 16/364,831

(22) Filed: Mar. 26, 2019

(65) Prior Publication Data

US 2019/0216300 A1    Jul. 18, 2019

Related U.S. Application Data

(63) Continuation of application No. PCT/IL2017/050930, filed on Aug. 21, 2017.

(60) Provisional application No. 62/401,177, filed on Sep. 29, 2016.

(51) Int. Cl.
| A61B 1/00 | (2006.01) |
|---|---|
| A61B 90/00 | (2016.01) |
| A61B 1/05 | (2006.01) |
| A61B 1/06 | (2006.01) |

(52) U.S. Cl.
CPC ...... *A61B 1/00183* (2013.01); *A61B 1/00179* (2013.01); *A61B 1/05* (2013.01); *A61B 90/361* (2016.02); *A61B 1/00006* (2013.01); *A61B 1/0011* (2013.01); *A61B 1/00055* (2013.01); *A61B 1/00078* (2013.01); *A61B 1/00177* (2013.01); *A61B 1/00181* (2013.01); *A61B 1/00193* (2013.01); *A61B 1/051* (2013.01); *A61B 1/0623* (2013.01)

(58) Field of Classification Search
CPC ............ A61B 1/00183; A61B 1/00071; A61B 1/00181
USPC .......................................................... 600/138
See application file for complete search history.

(56) References Cited

U.S. PATENT DOCUMENTS

| 3,818,902 | A * | 6/1974 | Kinoshita | .......... A61B 1/00096 600/109 |
|---|---|---|---|---|
| 6,371,909 | B1 * | 4/2002 | Hoeg | .................. A61B 1/00096 600/112 |
| 8,602,980 | B2 | 12/2013 | Bassan et al. | |
| 9,393,076 | B2 | 7/2016 | Fowler et al. | |
| 2002/0022767 | A1 * | 2/2002 | Dohi | .................. A61B 1/00183 600/173 |
| 2003/0032863 | A1 * | 2/2003 | Kazakevich | ....... A61B 1/00105 600/173 |

(Continued)

FOREIGN PATENT DOCUMENTS

WO    2012146664    11/2012

OTHER PUBLICATIONS

International Search Report PCT/IL2017/050930 Completed Nov. 8, 2017; dated Nov. 12, 2017 19 pages.

(Continued)

*Primary Examiner* — Aaron B Fairchild
(74) *Attorney, Agent, or Firm* — The Roy Gross Law Firm, LLC; Roy Gross

(57) ABSTRACT

The subject matter discloses a medical imaging device, comprising a rigid housing, at least two camera units located within said rigid housing, capturing images of different directions of view and a maneuver mechanism configured to change the physical orientation of a camera of the at least two camera units.

18 Claims, 15 Drawing Sheets

(56) References Cited

U.S. PATENT DOCUMENTS

| | | | |
|---|---|---|---|
| 2003/0097044 A1* | 5/2003 | Rovegno | A61B 1/00177 600/170 |
| 2004/0122290 A1* | 6/2004 | Irion | A61B 1/00181 600/171 |
| 2005/0038317 A1* | 2/2005 | Ratnakar | A61B 1/00105 600/101 |
| 2008/0081947 A1* | 4/2008 | Irion | A61B 1/00183 600/109 |
| 2008/0287736 A1 | 11/2008 | Yamazaki | |
| 2010/0022838 A1* | 1/2010 | Hoeg | A61B 1/00096 600/131 |
| 2012/0053407 A1 | 3/2012 | Levy | |
| 2012/0065476 A1 | 3/2012 | Choi | |
| 2013/0109916 A1 | 5/2013 | Levy | |
| 2013/0258081 A1 | 10/2013 | Akui et al. | |
| 2014/0221749 A1 | 8/2014 | Grant et al. | |
| 2014/0343358 A1 | 11/2014 | Hameed et al. | |

OTHER PUBLICATIONS

Written Opinion of the International Searching Authority PCT/IL2017/050930 dated Nov. 12, 2017 5 pages.

\* cited by examiner

RIGID MEDICAL SURGERY ILLUMINATING DEVICE

RELATED APPLICATIONS

This application is a Track-One-Continuation of PCT Patent Application No. PCT/IL2017/050930 having International filing date of Aug. 21, 2017, which claims the benefit of priority of U.S. Provisional Application No. 62/401,177 filed on Sep. 26, 2016. The contents of the above applications are all incorporated by reference as if fully set forth herein in their entirety.

FIELD OF THE INVENTION

The present invention generally relates to the field of medical instruments inserted to the body and more specifically to the field of medical instruments designed to capture images from inside the patient's body.

BACKGROUND OF THE INVENTION

An endoscope is a device with a light source attached to one end, utilized to look inside or inspect a region inside a confined area or a specific body cavity or organ. There are multiple different types of endoscopes, and depending on the site in the body and the type of procedures. In some cases, an endoscope may comprise one or more cameras utilized to capture the field of view of the endoscope. Such field of view may comprise any specific organ or a tissue which the person who operates the endoscope may desire to examine. The number of medical procedures and the medical procedure types has increased over the years and as of today, multiple medical procedures require different angels or viewpoints of examined tissues. Furthermore, while in some cases, one point of the examined tissue may meet the requirements of a single medical procedure, in other cases multiple views or angels may be required in a single medical procedure.

Endoscopy may be performed by a doctor or a surgeon and in most cases requires a tiny cut in the body, or inserting the endoscope via a natural opening in the body. Thus, minimizing the number of endoscopy tests, should be planed when endoscopy is considered for a patient.

SUMMARY OF THE INVENTION

The present invention discloses a medical imaging device, comprising a rigid housing, at least two camera units located within said rigid housing, capturing images of different directions of view, a maneuver mechanism configured to change the physical orientation of a camera of the at least two camera units.

In some cases, the at least two camera units comprise a front camera unit and a lateral camera unit. In some cases, the maneuvering mechanism maneuvers the lateral camera unit to capture a field of view at least partially overlapping with a field of view captured by the front camera unit. In some cases, the at least two camera units comprise a front camera unit and two lateral camera units. In some cases, the maneuvering mechanism maneuvers the two lateral camera units, such that each of the two lateral camera units captures a field of view at least partially overlapping with a field of view captured by the front camera.

In some cases, a camera unit of the at least two camera units is located in a camera compartment, located in a vicinity of an aperture in the rigid housing.

In some cases, the maneuver mechanism is connected to a hinge connected to a camera unit of the at least two camera units, wherein rotating the hinge results in changing the camera's direction of view.

In some cases, the maneuver mechanism is connected to two or more hinges connected to two or more camera units, simultaneously rotating the two or more hinges, thereby simultaneously changing the two or more camera's direction of view.

In some cases, the maneuver mechanism comprises a pulley controlled from outside the patient's body. In some cases, the maneuver mechanism comprises an adjusting rod sliding in the rigid housing. In some cases, the maneuver mechanism comprises a mechanism for locking and unlocking a camera unit's movement.

In some cases, the medical imaging device further comprising two or more lids configured to cover the two or more openings. In some cases, the two or more lids are transparent. In some cases, the two or more lids comprise light filters.

In some cases, the maneuver mechanism is controlled by a user, wherein the device further comprises a control unit.

In some cases, the maneuver mechanism is controlled by a software algorithm, wherein the device comprises an input unit configured to receive properties used by the software algorithm to maneuver the two or more camera units.

In some cases, the maneuver mechanism has a notification element to notify the user about the camera's direction of view. In some cases, the rigid element is made of a single rigid sheet of material. In some cases, the maneuver mechanism is physically connected to the at least two camera units.

The present invention also discloses a method for producing a medical imaging device, comprising receiving a specific medical procedure imaging requirement, said requirement comprises a field of view defined by a distance and direction of an object from a tip of the medical imaging device, locating at least two camera units within a rigid housing of the medical imaging device, positioning at least two camera units such that the within at least two camera units capture the field view when located in the medical imaging device, affixing the at least two camera units to its physical location.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawing.

DETAILED DESCRIPTION OF THE INVENTION

The present invention discloses a medical imaging device equipped with cameras designed to be inserted into the body through a hollow organ, or cavity of the body. The medical imaging device may be utilized to view internal organs and vessels of a body at different angels and with diverse optional fields of view, while the two or more cameras are positioned in a single rigid housing. The rigidity is defined by the housing elements remain still. Such housing elements may be transparent windows that enable the cameras to capture images and video and the MSID handle, as well as the MSID body. Thus, the external elements of the MSID do not move, while the camera modules move inside the housing to enable a dynamic field of view. The rigidity may also be defined by not having moving joints, in case the housing is assembled of a plurality of housing elements connected in series.

Figure 1:
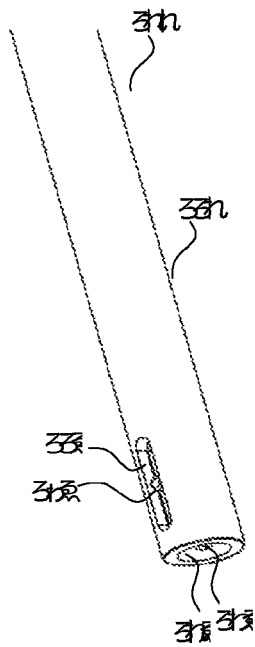
FIG. 1 demonstrates a medical imaging device comprises at least one camera, according to exemplary embodiments of the present invention.

FIG. 1 demonstrates a medical imaging device comprises at least one camera, according to exemplary embodiments of the present invention. Medical imaging device 100 comprising a cylindrical shaped tube 110 used to be inserted into a body through a hollow organ, or cavity of the patient's body. The medical imaging device 100 may comprise at least one internal camera located either in the front or in the lateral section of the tube 110.

The tube 110 can be made of a material such as plastic, rubber, synthetic rubber, metal, stainless steel and the like. In some cases, the tube 110 may be made of a composition, or assembly of two or more materials. For example, tube 110 may be made of metal and covered with a plastic or glass layer.

The tube 110 comprises two cameras, camera 125 located at the lateral section of cylindrical shaped tube 110 and camera 135 in located at the front of the cylindrical shaped tube 110. The cameras 125 and 135 may be of any camera type used to support medical procedure which require imaging device inserted to a body, such as x-ray camera, video camera, digital image camera, and the like.

The tube 110 may be made of a single housing, such that the electricity is not required to pass from one housing to another and there are no external moving joints in various sections of the tube 110. Further, the two or more cameras 125, 135 of the medical imaging device 100 of the present invention are located in the same housing.

The tube 110 also comprises an aperture 105 which allows camera 135 to capture a field of view at the front section of the device 100. The aperture 105 may be round shaped. The camera space may be defined inside the tube 110, defined by the body of the imaging device 105. In some cases, the aperture 105 may also comprise a socket designed to host a transparent lid configured to cover the aperture 105 in order to support the camera 135 functioning. Such functioning may be capturing the field of view in the front direction of the device 100, tilt the camera 135 upward or downward, rotate, or any other movements required to be performed by a camera in order to facilitate said medical imaging during the medical procedure. In some cases, the aperture 105 may be covered with a lens configured to improve the camera 135 functionality, for example to broaden the camera field of view from 70 degrees to 85 degrees.

The cylindrical shaped tube 110 also comprises a lateral aperture 115 which supports the functioning of camera 125 in similar manner as aperture 105 supports camera 135. The lateral aperture 115 may also comprise a transparent lid which can cover the lateral aperture 115. In some cases, the camera 125 may be located at the middle of the lateral camera compartment aperture 115. In some other cases, camera 125 may be located closer to one of the ends of lateral aperture 115. For example, camera 125 can be located in some point along the lateral aperture 115, closer to the left end (shown as the upper end in FIG. 1), or closer to the right end (shown as the lower end in FIG. 1) of lateral aperture 115.

In some embodiments of the present invention, the tube 110 may also comprise a light source to illuminate the field of view of the medical imaging device 100. Such light source may be an output of a fiber optic module, a LED, or any other illumination device utilized for said medical procedures.

Figure 2A:
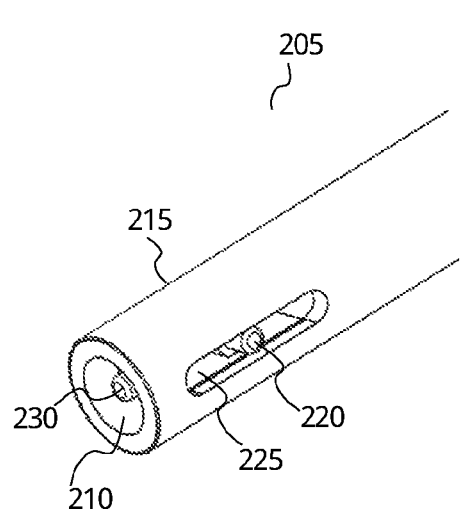
FIGS. 2A and 2B show two corresponding sides of a medical imaging device with 3 cameras, according to exemplary embodiments of the present invention.
Figure 2B:
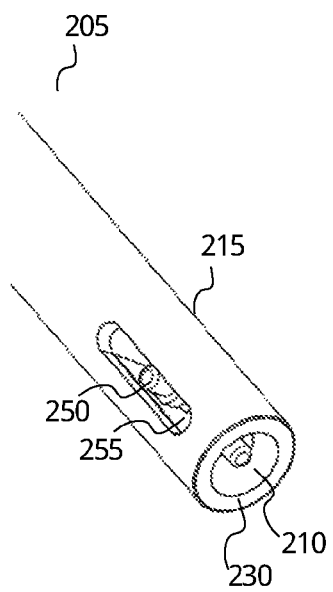

FIGS. 2A and 2B show two corresponding sides of a medical imaging device having 3 cameras, according to exemplary embodiments of the present invention. FIG. 2A shows a medical imaging device 205 comprises a cylindrical shaped tube 215, front camera 230 and lateral camera 220 which can be utilized in the medical procedures. In some cases, lateral camera 220 is located at the center of lateral aperture 225. In other cases, lateral camera 220 may be located closer to one of the sides of the elongated aperture 225. In some other cases, lateral camera 220 may be able to tilt up or down inside the lateral aperture 225. The field of view captured by lateral camera 220 may change according to tilting or otherwise maneuvering the lateral camera 220 inside the lateral aperture 225.

The medical imaging device 205 also comprises a front aperture 210 configured to support the functioning of front camera 230. In some embodiments of the present invention, the medical imaging device 205 may be designed to support an operation of replacing the front camera 230 and/or lateral camera 220 with cameras of a different type. For example, in case front camera 230 is a video camera, a user utilizing the medical imaging device 205 may be able to replace the front camera 230 with an imaging camera, or with an x-ray camera.

FIG. 2B shows the corresponding side of the medical imaging device 205 with a cylindrical shaped tube 215, camera 250 which can be utilized in medical procedures as elaborated above. In FIG. 2B, the cylindrical shaped tube 215 may comprise an additional lateral camera 250, located at additional elongated aperture 255. The additional lateral camera 250 may also be able to tilt up or down or laterally. The term laterally is defined in the axis from front camera 230 towards the handle (not shown) of the device 205. The cameras of the medical imaging device 205 may be attached to the device in a single point of contact, enabling maneuver of the cameras at 360 degrees. Additional lateral camera 250 can also be located in different places along the additional elongated aperture 255.

Figure 3A:
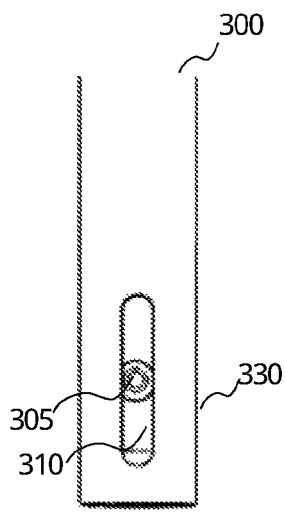
FIGS. 3A and 3B show two positions of a camera within a medical imaging device, according to exemplary embodiments of the present invention.
Figure 3B:
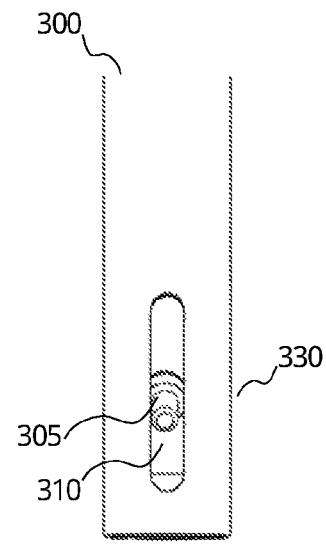

FIGS. 3A and 3B show two positions of a maneuverable camera within a medical imaging device, according to exemplary embodiments of the present invention. FIG. 3A shows a medical imaging device 300 comprising a cylindrical shaped tube 330, a lateral camera 305 and a lateral aperture 310. Lateral camera 305 may be located in the middle of lateral aperture 310 and directed forward. The term forward may be defined as perpendicular to the imaginary line extending between the tip and the handle of the medical imaging device 300. The lateral camera 305 may have a direct field of view, expanded to the side of the cylindrical shaped tube 330. In some cases, cylindrical shaped tube 330 may comprise additional cameras. For example, cylindrical shaped tube 330 may comprise an additional camera in the front section or in the lateral section at another location or direction than the lateral camera 305.

FIG. 3B shows another position of lateral camera 305 in medical imaging device 300, in which camera 305 is pointed toward the front side of the cylindrical shaped tube 330 (shown as pointing downwards). The lateral camera 305 may have a different field of view than the front camera (not shown in the image). In some cases, the field of view of lateral camera 305 may be overlapped with field of view of another camera positioned in cylindrical shaped tube 330. In some other cases, the portion of the field of view part which overlaps with another field of view may also be changed as a result of the different direction of view of the lateral camera 305.

Figure 3C:
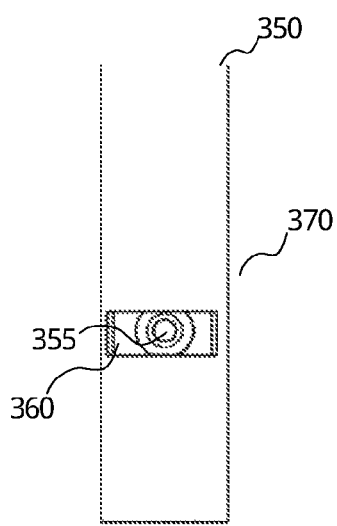
FIGS. 3C and 3D show two horizontal positions of a maneuverable camera within a medical imaging device, according to exemplary embodiments of the present invention.
Figure 3D:
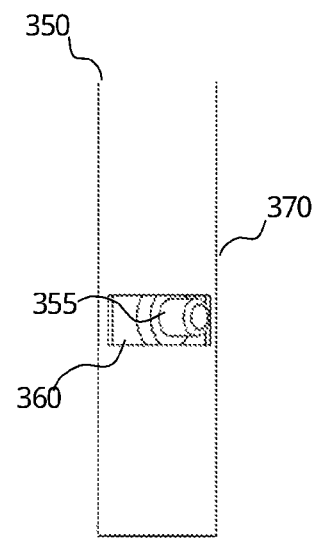

FIGS. 3C and 3D show two horizontal positions of a maneuverable camera within a medical imaging device, according to exemplary embodiments of the present invention. FIG. 3C shows a medical imaging device 350 comprising a cylindrical shaped tube 370, a lateral camera 355 and a lateral aperture 360. Lateral camera 355 may be located in the middle of lateral aperture 360 and directed forward. In some cases, cylindrical shaped tube 370 may comprise additional cameras, for example in the front section or in the lateral section of the cylindrical shaped tube 370. The additional camera may have a different location or direction than the lateral camera 355.

FIG. 3D shows a different horizontal position of lateral camera 355 in medical imaging device 350, in which lateral camera 355 is pointed toward the left side of the lateral aperture 360. In some medical procedures, the user may configure the lateral camera 355 to point to a different direction along the lateral aperture 360. The lateral camera 355 may have a different field of view than the front camera (not shown in this image). In some cases, the field of view of lateral camera 355 may be overlapped with a field of view of another camera positioned in cylindrical shaped tube 370. In some other cases, the portion of the field of view which overlaps with another field of view may also be changed as a result of the different direction of view of the lateral camera 355. The angle of the direction of view of the lateral camera 355 may be maneuvered during the medical procedure using a mechanism disclosed in details below.

Figure 4A:
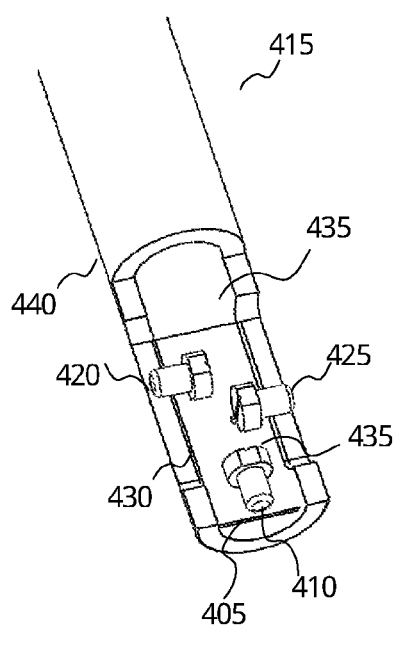
FIGS. 4A and 4B show different views of a cross-section of a medical imaging device, according to exemplary embodiments of the present invention.
Figure 4B:
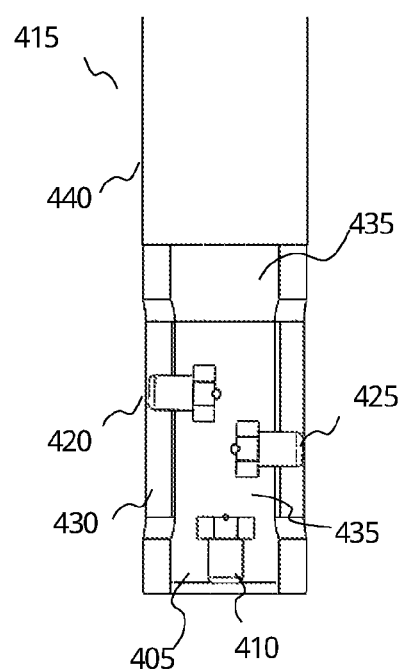

FIGS. 4A and 4B show different views of a cross-section of a medical imaging device, according to exemplary embodiments of the present invention. FIG. 4A shows an angled view of a cross-section of medical imaging device 415. The medical imaging device 415 comprises a cylindrical shaped tube 440, which in some cases can be provided in a single, unified and homogenous unit. In some cases, the homogenous tube 440 cannot bend or arranged in a round or angle shaped tube. The cylindrical shaped tube 440 comprises 3 cameras, camera 410, 420, and 425 which are designed to capture the field of view of a medical imaging device 415. First lateral camera 420 is placed within elongated aperture 430 and configured to be tilted up or down along the elongated aperture 430. In some cases, first lateral camera 420 may be able to rotate clockwise or counter-clockwise. Cylindrical shaped tube 440 also comprises a hollow space 435 that can be used to host cables or wires required for the functionality of the medical imaging device 415. For example, in some cases, cables deliver electrical power or wires which transmit data and connected to the camera may be located in hollow space 435. In some cases, hollow space 435 may comprise electrical components such as electrical circuit boards, or any other electrical components required for the standard operation of the medical imaging device 415.

Cylindrical shaped tube 440 also comprises second lateral camera 425 located within elongated aperture 435 and functioning in similar manner as first lateral camera 420. The cylindrical shaped tube 440 also comprises a front camera 410 located in the front aperture 405. Front aperture 405 may be round shaped. Front camera 410 is placed in the front of the medical imaging device 415 and configured to capture the front section of the field of view of medical imaging device 415. In some cases, the field of view captured by front camera 410 may be overlapped with the field of view being captured by first lateral camera 420, or with the field of view being captured by second lateral camera 425. In some embodiments of the present invention, the overlapped parts within the field of view of the cameras may be used by a user operating the medical imaging device 415 to view the same object from different directions or different distances, or via different camera types. For example, a user operating the medical imaging device 415 may view a part of a tissue through camera 410. Then, the user operating the medical imaging device 415 may utilize the field of view captured by second lateral camera 425 in order to view the same tissue part from a different angle or distance. In some embodiments of the present invention, the user may be able to change the position of cameras 420, 425 in order to enlarge the field of view, change the angle of the field of view, narrow the viewing, and the like. In some other embodiments of the present invention, the positions of the cameras, 425, 420 and 410 may be fixed and the user operating the medical imaging device 415 may not be able to change the field of view.

FIG. 4B shows a straight view of a cross-section of medical imaging device 415. Medical imaging device 415 comprises a cylindrical shaped tube 440, which in some cases can be provided in a single, unified and homogenous unit which cannot bend or arranged in a round or angle shaped tube. The cylindrical shaped tube 440 comprises a camera 425 located within elongated aperture 435 and functioning in similar manner as camera 420, and camera 410 located in the round aperture 405. The cylindrical shaped tube 440 is designed to house the cameras 410, 420, and 425 in a single and integral unit. The cylindrical shaped tube 440 also comprises lateral camera compartments 430 and 435 which provide the lateral cameras 425, and 420 the needed leeway to tilt up or down along the elongated camera compartments. In some cases, lateral cameras 420, 425 have a single point of contact to the body of the imaging device 415, which enables maneuvering the cameras 420, 425 at 360 degrees around the single contact point.

In some cases, the tilt movement of the camera may be performed during the medical procedures, in order to change, adjust, improve, or tune the field of view captured by the 3 cameras 420, 425 and 410. For example, in case a user inserts the medical imaging device 415 into a body as a part of a medical procedure, the user may be able to move and adjust the positions of cameras 420, 425 and 410 in order to adjust the field of view of an examined tissue. The user may also be able to see the captured field of view on an external screen. In some cases, the user may capture views in an image file format. In some other cases, the position and the direction of the cameras 420, 425 and 410 may be determined in advance, before the medical procedure starts, and the person who performs the medical procedure may not be able to change the camera positions. In some cases the device will have a notification means to notify the user about the camera's position. Said notification mechanism can be an electrical or mechanical. For example, the user may press on a button on the device and an illustration will be displayed on the monitor.

Figure 5A:
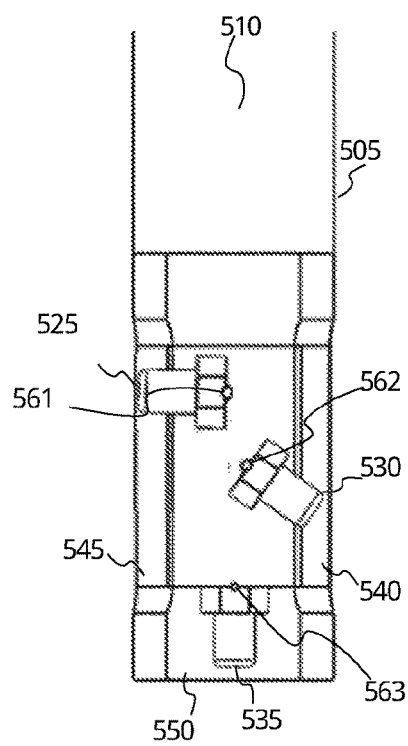
FIGS. 5A, 5B, and 5C show alternative settings of the cameras in medical imaging device, according to exemplary embodiments of the present invention.
Figure 5B:
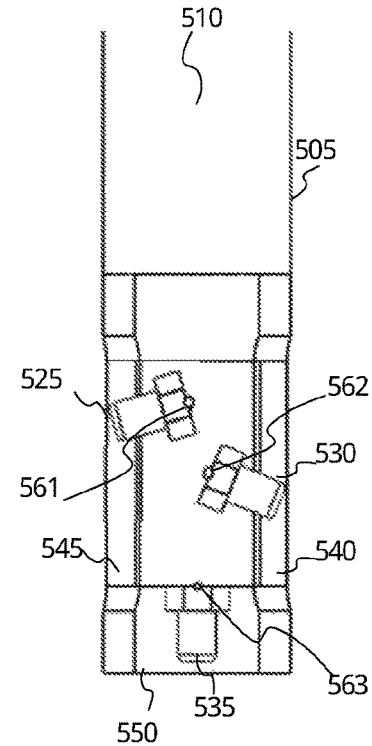
Figure 5C:
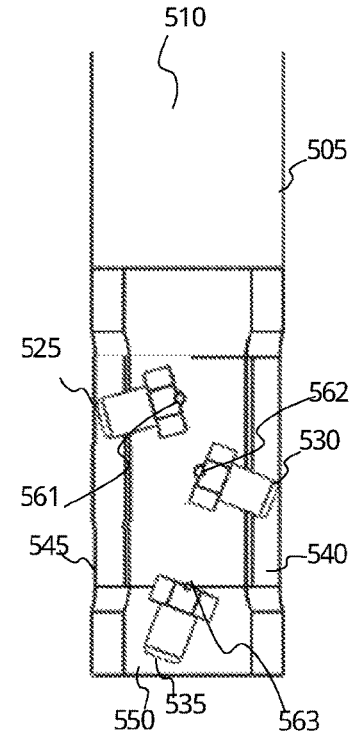

FIGS. 5A, 5B, and 5C show alternative settings of the cameras in a medical imaging device, according to exemplary embodiments of the present invention. FIG. 5A shows medical imaging device 510, comprises cylindrical shaped tube 505, disclosing the positions of 3 cameras 525, 530, and 535, located within cylindrical shaped tube 505. Cylindrical shaped tube 505 also comprises lateral camera compartments 540, and 545 to support the positions and the functionality of camera 525, and 530, as disclosed above.

Camera 530, located within cylindrical shaped tube 505, can be configured with the front of the camera pointing down, towards the front camera 535. The camera 530 comprises a hinge 562 used to set camera 530 in a fixed point within the cylindrical shaped tube 505 and to enable the rotation movement of the camera 530.

The cylindrical shaped tube 505 also comprises a hinge 561 utilized to set the camera 525 to a fixed point and enable the rotation movement, in similar manner as hinge 562 fixes the camera 530. Similarity, hinge 563 used to set the camera 535 to a fixed point and enable the rotation movement, in similar manner as hinge 562 fixes the camera 530. In some cases, the user who operates the medical imagining device 510, may be able to rotate the camera 535 clockwise or counterclockwise. In some other cases, a user may be able to change the position of camera 530 during a medical procedure in order to change the field of view of the medical imaging device 510. Such changes may be, tilt up, tilt down, rotate the cameras, adjust the focal point, and the like. In some cases, the user may select a fixed setting of the camera setting such as the camera settings in FIG. 5A, 5B or 5C. In such cases, changes in the field of view may be enabled by replacing the medical imaging device 510 with a device having a desired fixed camera setting. For example, in case a user utilizes the medical imaging device 510 as shown in FIG. 5A, the user can change the field of view by replacing the medical imaging device 510 with another medical imaging device comprising the camera setting shown in FIG. 5C.

FIG. 5B shows the medical imaging device 510 with alternative setting of the cameras 525 and 530. FIG. 5B shows the cylindrical shaped tube 505 comprises cameras 525, 530, and 535. Camera 530 is rotated clockwise on hinge 562 and pointing downwards, towards front camera 535. Camera 525 is rotated on hinge 561 and pointed down, towards front camera 535. In some embodiments of the present invention the positions of the cameras 525, 530, and 535 can be fixed with no option for the user to change, or adjust field of view. In some cases, in which the camera positions are fixed with no option to change them by a user, the user may replace the entire medical image device and use an alternative medical image device with different camera positions, in order to change the viewing filed. The cylindrical shaped tube 505 also comprises a front aperture 550 and lateral aperture 540 and 545.

FIG. 5C shows a possible embodiment of the medical imaging device 510 with front camera 535 rotated on hinge 563. Front camera 535 is rotated clockwise on hinge 563 and pointed to the right. FIG. 5C also shows the cylindrical shaped tube 505 and cameras 525, and 530. In some cases, the field of view of front camera 535 may overlap with the field of view of camera 525, or with the field of view of camera 530. For example, in case a user utilizing the medical imaging device wants to acquire an image of a watched object in a different angle or the user wants to obtain a larger or small overall field of view for example to achieve an image of the entire surgical view. The user may change one of the camera positions till the object is captured by more than one camera. Such change may be rotation of the camera upward or downward, turning the camera around, changing the focal point of the lenses, and the like. The front aperture 550 may comprise a socket designed to host a lid of transparent matter, for enabling the cameras to capture images of the vicinity of the medical imaging device.

Figure 6:
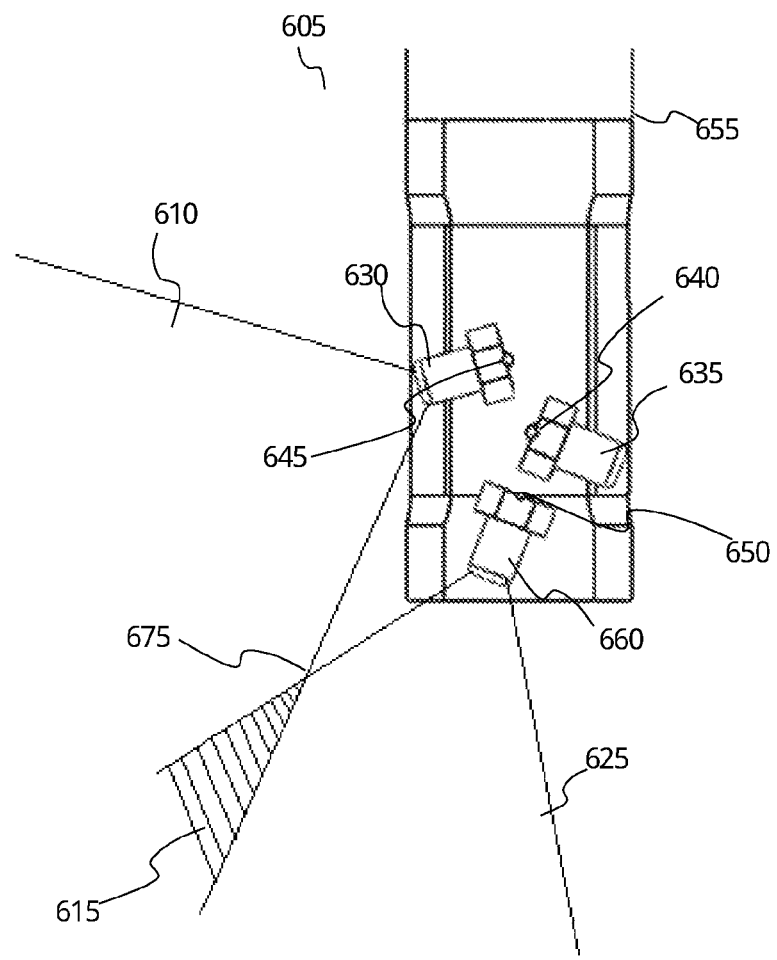
FIG. 6 shows a medical imaging device and cameras which have an overlap between the fields of view of two cameras, according to exemplary embodiments of the present invention.

FIG. 6 shows a medical imaging device and cameras which have an overlap between the fields of view of two cameras, according to exemplary embodiments of the present invention. Medical imaging device 605 comprises a cylindrical shaped tube 655. The cylindrical shaped tube 655 comprises 3 cameras, camera 630, which can be rotated on hinge 645, camera 635 which can be rotated on hinge 640, and camera 660 which can be rotated on hinge 650.

In some cases, the cameras 630, 635, 660 may be static and non-movable, as they maintain a certain field of view once inserted into the cylindrical shaped tube 655. That is, the orientation of the cameras 630, 660 may be static and non-movable, which results in a constant camera configuration for each overlapping field of view. For example, the overlapping field of view 615 may be viewed by camera 660 in an angle of 8 degrees from the elongated axis of the medical imaging device 605 and viewed by camera 630 in an angle of 24 degrees from the elongated axis of the medical imaging device 605. FIG. 6 shows field of view 610 captured by camera 630. The area defined by field of view 610 can be changed in accordance with changing in the settings of camera 630. Such settings may comprise changing the focal point of camera 630, changing the physical position of camera 630, changing the distance of the objects captured by the camera 630, changing the direction of view captured by camera 630, broadening the boundaries of the field of view, and the like. For example, a user can change the focal point of camera 630 and tilt it down. As a result, the objects captured by camera 630 may change and the distance of the objects captured by camera 630 may also change. FIG. 6 also shows the field of view 625 captured by camera 660. Camera 660 can rotate and change the boundaries of the field of view. For example, camera 660 can rotate clockwise and change the boundaries of the field of view 625 to the right. In some cases, the user of the medical imaging device 605 may configure the boundaries of the field of views 625 and 610 to overlap with each other, such that field of view 615 is defined, which illustrates the overlapping fields of view between camera 630 and camera 660. In some cases, a user utilizing the medical imaging device 605 may configure the cameras 630, and 660 with an overlapping fields of view. For example, in case a user examines an object within a human body, the user may configure the cameras to capture the same object from two different angels, or in some cases the user may configure one of the cameras to allow an overall wider viewing angle of the device without compromising the image quality due to distortion. The objects captured by the cameras may be transmitted by the medical imaging device 605 to remote screens or other devices. The overlapping field of view 615 may be defined by the closest point 675 captured by both cameras 630, and 660. In some cases, the distance and direction of the closest point 675 from the tip of the medical imaging device 605 is inputted into a computerized system, which uses the input related to the closest point 675 and to the overlapping field of view 615 in order to determine the position and orientation of the cameras 630, 660 in the medical imaging device 615. The overlapping field of view may be calculated at the horizontal or diagonal fields.

Figure 7A:
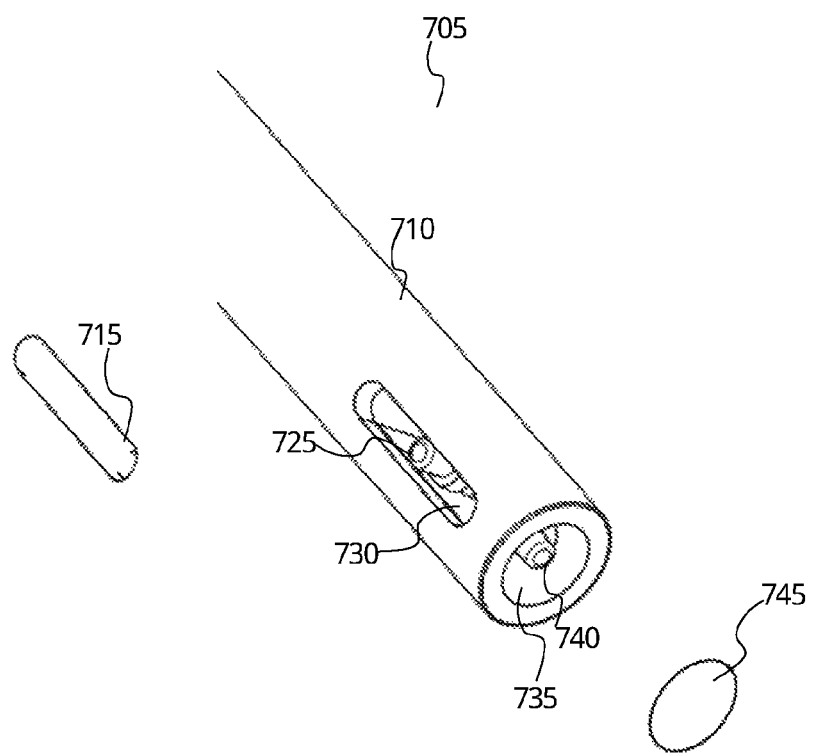
FIG. 7A shows a lateral view of a medical imaging device with two openings and two lids of the openings, according to exemplary embodiments of the present invention.

FIG. 7A shows a lateral view of a medical imaging device with two camera compartments and two lids of the camera compartments, according to exemplary embodiments of the present invention. Cylindrical shaped tube 710 comprising a lateral camera 725, an elongated lateral aperture 730, a front camera 740 and a front aperture 735. Lateral camera 725 and front camera 740 are designed to capture the fields of view according to a predefined medical procedure. The elongated lateral aperture 730 located at the lateral section of the cylindrical shaped tube 710 is designed to host a lateral lid 715. Lateral lid 715 can close hermetically the elongated lateral aperture 730 in order to support the functioning of lateral camera 725. Such functioning may be capturing the field of view in the lateral vicinity of the device, tilt up or down, rotate, or any other movements required to be performed by a camera in order to facilitate said medical procedures. In some cases, lateral lid 715 can comprise a light filter configured to cover the elongated lateral aperture 730. Such light filter can be a color filter, a wavelength filter, a light diffuser, a beam splitter or any other filter that may be used for a certain medical procedures performed using the medical imaging device 705. The cylindrical shaped tube 710 also comprises a front lid 745 designed to be inserted into round aperture 735 in order to support the functionality of front camera 740, in the same fashion as lateral lid 715 supports the functionality of lateral camera 725. In diverse possible embodiments of the present invention, the front lid 745 may be in different shapes such as a round shape, elliptic shape, and the like, in order to appropriately support the functionality of front camera 745. Front lid 745 may also be designed to be added with a light filter in similar fashion as lateral lid 715. In some cases, the front lid 745 may be designed to seal the front aperture 735, and the lateral lid 715 may be designed to seal the lateral aperture 730 in order to provide a hermetic barrier between the human body and the internal components of the medical imaging device 705. In such cases, front lid 745 and lateral lid 715 may be also designed to go through a sterilization process such as autoclave. The front lid 745 and lateral lid 715 may be biocompatible barriers which prevent any interaction between the internal components of the medical imaging device 705 and the outer environment in which the medical imaging device 705 operates.

In some embodiments of the present invention, the filters in lateral lid 715 and/or filters in front lid 745 may be replaceable filters so that a user utilizing the medical imaging device 705 may mount various filters on the elongated lateral aperture 730, or on the front aperture 735, in order to capture different aspects or views during said medical procedure. For example, a user may cover the elongated lateral aperture 730 with a lid comprising a wavelength filter in order to capture specific aspect of a tumor during a medical procedure. Then, the user may replace the lid with a transparent lid, in order to capture different aspects of the same tumor, during said medical procedure. In some cases, the medical imaging device 705 may be designed to host a non-replaceable lid. In such cases, the user of the medical imaging device 705 may need to utilize multiple medical imaging devices during said medical procedure. For example, a user utilizing a medical imaging device 705 comprising a lid 745 with a wavelength filter may require to change the wavelength filter with a transparent lid. Thus, the user may pull the medical imaging device 705 out of the patient's body and replace the medical imaging device comprising a wavelength filter lid with a medical imaging device comprising a transparent lid. In some cases, the medical imaging device 705 may provide with an option to add filters such as the filters mention above, on the top of the lateral lid 715 and/or on the top of the front lid 745.

Figure 7B:
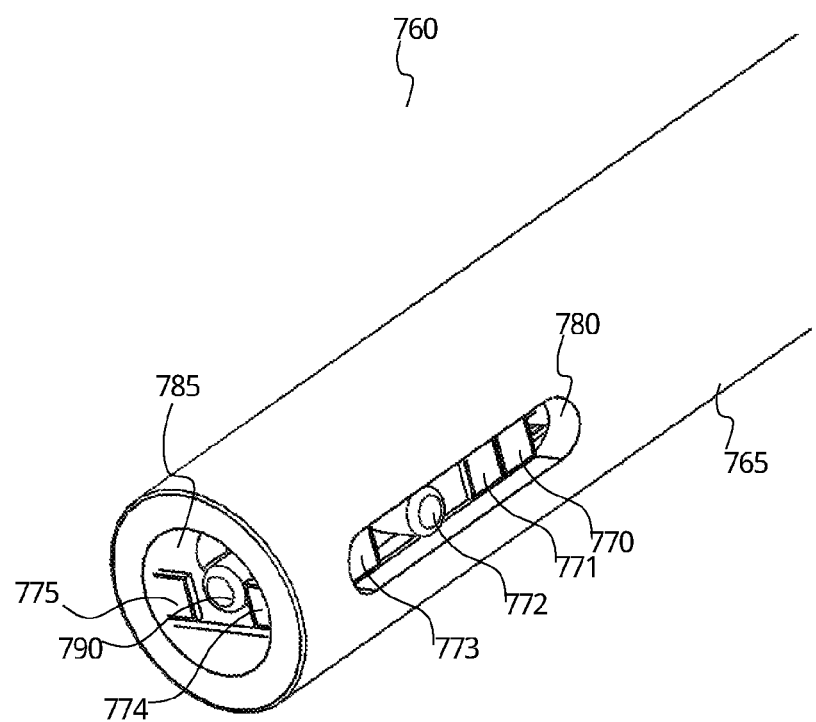
FIG. 7B shows a lateral view of the medical imaging device comprises a light source to illuminate the field of view of the medical imaging device, according to exemplary embodiments of the present invention.

FIG. 7B shows a lateral view of the medical imaging device comprises a light source to illuminate the field of view of the medical imaging device, according to exemplary embodiments of the present invention. FIG. 7B shows a medical imaging device 760 comprises a cylindrical shaped tube 765, front camera 790 and lateral camera 772 which can be utilized in the medical procedures. In some cases, lateral camera 772 is located at the center of lateral aperture 780. In other cases, lateral camera 772 may be located closer to one of the sides of the lateral aperture 780. In some other cases, lateral camera 772 may be able to tilt left or right inside the lateral aperture 780. The field of view captured by the device 760 may change according to tilting or otherwise maneuvering the lateral camera 772 inside the lateral aperture 780. The lateral aperture 780 also comprises light sources 770, 771, and 773 designed to illuminate the field of view of the medical imaging device 760. Such light sources 770, 771, and 773 may be an output of a fiber optic module, a LED, or any other illumination device utilized for said medical procedures.

The medical imaging device 760 also comprises a front aperture 785 configured to support the functioning of front camera 790. In some embodiments of the present invention, the medical imaging device 760 may be designed to support an operation of replacing the front camera 790 and/or lateral camera 772 with cameras of a different type. The front aperture 785 also comprises light sources 774 and 775 designed to illuminate the field of view of the front camera 790, in similar fashion as light sources 770, 771, and 773.

Figure 8:
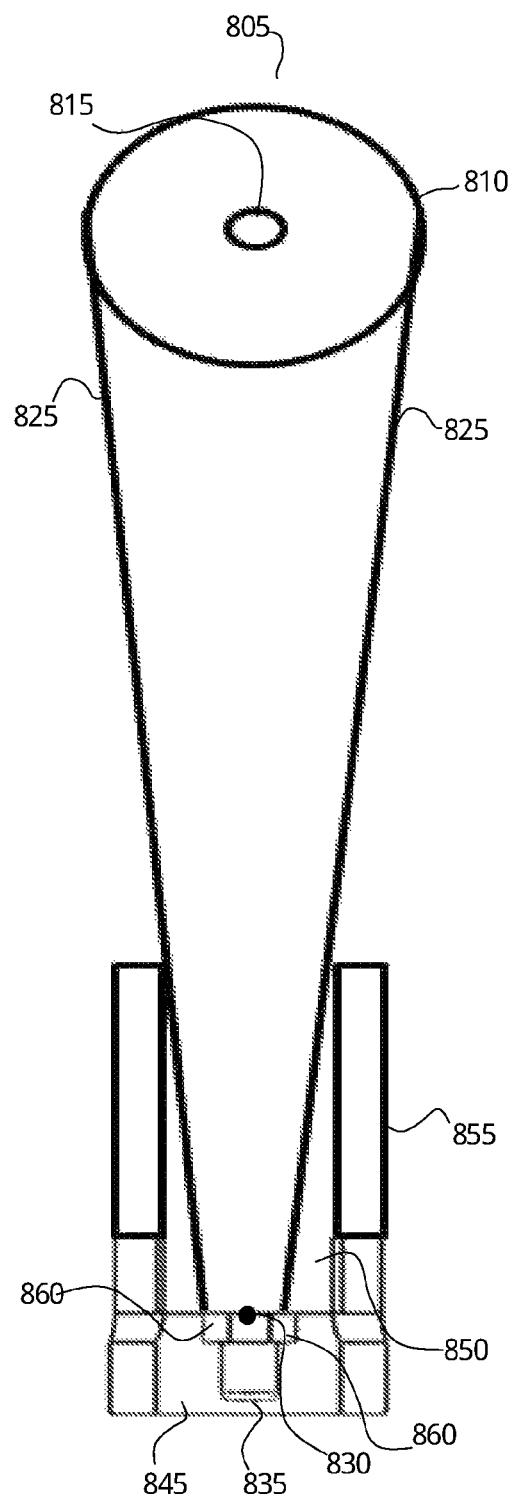
FIG. 8 shows a cross-section of a medical imaging device comprising a camera with a technique to change the field of view of said camera, according to exemplary embodiments of the present invention.

FIG. 8 shows a cross-section of a medical imaging device comprising a camera with a technique to change the field of view of said medical imaging device, according to exemplary embodiments of the present invention. FIG. 8 shows a cross-section of a medical imaging device 805 comprising a front camera 835. Front camera 835 may be able to rotate left or right, on hinge 830 in order to move and change the field of view of front camera 835. The medical imaging device 805 also comprises a cylindrical shaped tube 855, and a front aperture 845 in which the front camera 835 is located. The medical imaging device 805 further comprises a pulley 810 mounted on pulley hinge 815 and designed to rotate right or left. The medical imaging device 805 also comprises a rotation belt 825 that surrounds the pulley 810. The rotation belt 825 is connected to the front camera 835 via camera base 860 in order to translate the rotation movements of pulley 810 to the rotation movements of the front camera 835. In some cases, the rotation belt 825 can be made of wires, a chain, a rubber, and the like. In some cases, the camera base 860 is a wall of the aperture 845. For example, pulley 810 can be rotated clockwise or counterclockwise around pulley hinge 815 and thereby move the rotation belt 825 upward or downward in linear movements. Thus, in case the rotation belt 825 is connected to the camera base 860, the front camera 835 may move clockwise or counterclockwise, in accordance with the linear movements of rotation belt 825. Movement of the front camera 835 results in changing the field of view captured by the front camera 835, as the manipulation of the position of the front camera 835 may be performed outside the patient's body mechanically by the user or electrically, by controlling the pulley's movement using an electronic motor. For example, the pulley mechanism may be connected to an electrical motor such as a step motor, said step motor is configured to rotate a predefined number of steps upon an electrical signal input generated by the user in means of a button press.

The cylindrical shaped tube 855 also comprises a hollow space 850 that can be used to host cables, wires or other components such as the rotation belt 825, required to the functionality of the medical imaging device 805.

Figure 9:
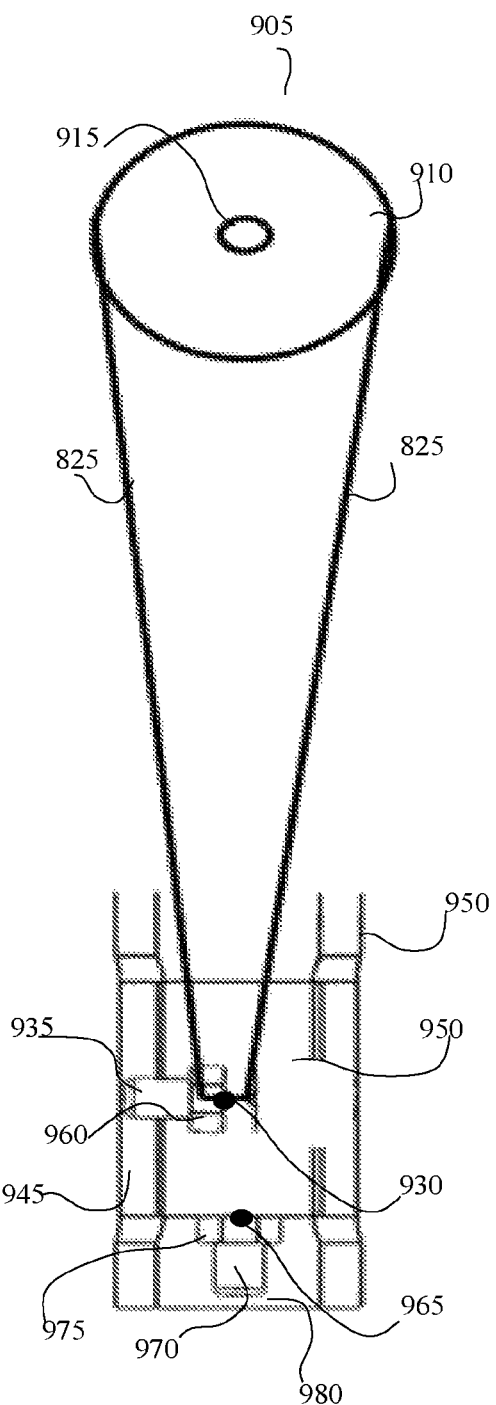
FIG. 9 shows a cross-section of a medical imaging device comprising a front camera and a side camera with a technique to change the field of view of one of the cameras, according to exemplary embodiments of the present invention.

FIG. 9 shows a cross-section of a medical imaging device comprising a front camera and a lateral camera with a mechanism to change the field of view of one of the medical imaging device, according to exemplary embodiments of the present invention. Medical imaging device 905 comprising a front camera 970 and a lateral camera 935. The lateral camera 935 may be able to rotate left or right, on hinge 930 in order to move and change the direction of view captured by the lateral camera 935. The medical imaging device 905 also comprises a cylindrical shaped tube 955, and a lateral aperture 945 in which the lateral camera 935 is located. The medical imaging device 905 also comprises a front aperture 980 in which the front camera 970 is located. Medical imaging device 905 further comprises a pulley 910 mounted on pulley hinge 915 and designed to rotate right or left. The medical imaging device 905 also comprises a rotation belt 925 that surrounds the pulley 910. The rotation belt 925 also has two ends connected to the lateral camera 935 via camera base 960 and hinge 930, in order to translate the rotation movements of pulley 910 to rotation movements of the side camera 935. In some cases, the rotation belt 925 can be made of wires, a chain, a rubber, and the like. In some cases, one of the ends of rotation belt 925 may be connected to hinge 930 and the other end of rotation belt 925 may be connected to camera base 960. For example, pulley 910 can be rotated clockwise or counterclockwise around pulley hinge 915 and thereby move the rotation belt 925 upward or downward in linear movements. Thus, the lateral camera 935 may point upward or downward, in accordance with the linear movements of rotation belt 925.

The cylindrical shaped tube 955 also comprises a hollow space 950 that can be used to host cables, wires or other components such as the rotation belt 925, required for the functionality of the medical imaging device 905. The cylindrical shaped tube 955 further comprises front camera 970 with front camera base 975, which can be rotated on hinge 965, and a front aperture 980 for hosting front camera 970. In some cases, a user utilizing the medical imaging device 905 may have the option to change the direction of view of front camera 970, in the same manner as in lateral camera 935. The pulley 910 may be controlled mechanically by the user or electrically, by controlling the pulley's movement using an electronic device.

Figure 10:
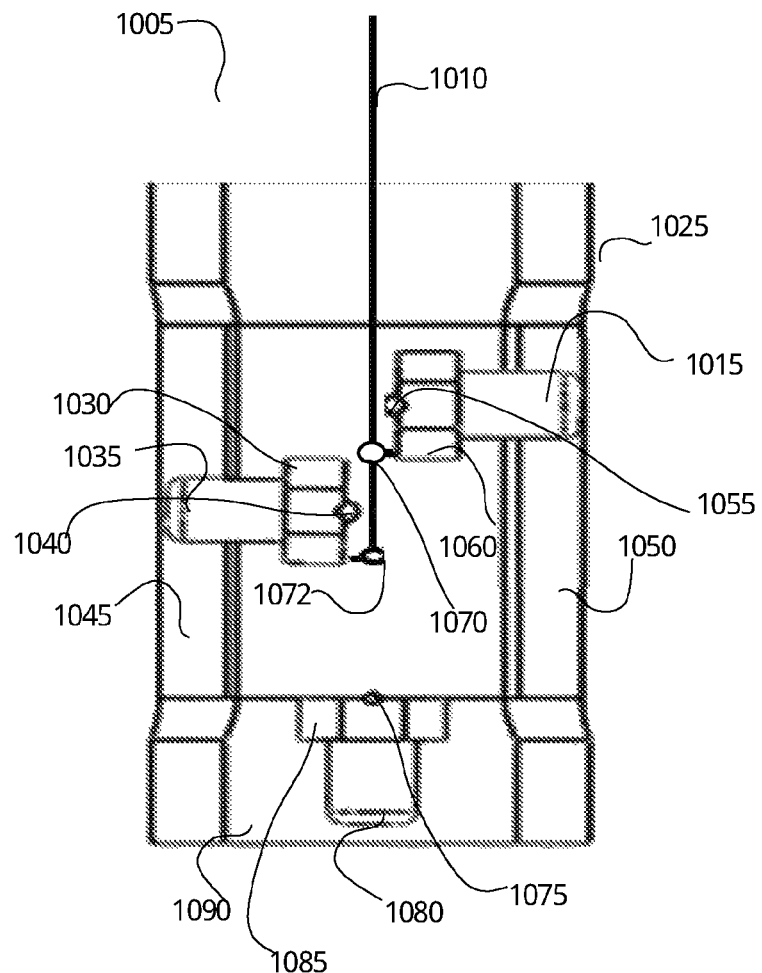
FIG. 10 shows a medical imaging device comprising 3 cameras and an adjusting rod to configure the fields of view of the camera, according to exemplary embodiments of the present invention.

FIG. 10 shows a medical imaging device comprising 3 cameras and an adjusting rod to configure the fields of view of the medical imaging device, according to exemplary embodiments of the present invention. Medical imaging device 1005 has a cylindrical shaped tube 1025 and 3 cameras with an adjustable direction of view. The medical imaging device 1005 comprises adjusting rod 1010 designed to change the orientation of lateral camera 1035 and lateral camera 1015. The cylindrical shaped tube 1025, contains a front camera 1080 configured to capture the field of view in the front vicinity of the medical imaging device 1005. The front camera is located in the front aperture 1090. Front camera 1080 is mounted on hinge 1075 via camera base 1085. In some cases, the hinge 1075 can be used to support the rotation movements of front camera 1080. The lateral camera 1015 is mounted on hinge 1055 via camera base 1060. Lateral camera 1035 is mounted on hinge 1040, via camera base 1030 in similar manner as lateral camera 135 is mounted on hinge 1055 via camera base 1060.

In some embodiments of the present invention, the adjusting rod 1010 can be connected to hinge 1070 in order to change the physical orientation of the lateral camera 1035 and lateral camera 1015. Hinge 1070 can also be connected to camera base 1060. Hinge 1072 connects the hinge 1070 to the camera base 1030 and enables converting the hinge's 1070 movement to movement of the camera base 1030. Thus, the adjusting rod 1010 can be pulled out or in and thereby direct the lateral camera 1035 and lateral camera 1015 upwards or downwards, respectively. That is, when the adjusting rod is pushed towards the front cameras, the field of view of lateral cameras 1015, 1035 is upwards, away from the field of view of the front camera. In some cases, the adjusting rod 1010 may comprise a mechanism used to attach and detach from the camera bases 1030, 1060. This way, the user of the device may insert the adjusting rod 1010 and decide whether to use the rod to change the field of view of the lateral cameras 1015, 1030 or the field of view of the front camera.

In some embodiments of the present invention the direction of view of the side and the front camera in a medical imaging device may be configured and fixed without any ability to change them by the user. For example, a medical imaging device 1005 may be produced with one side camera 1035 pointing down towards the front of the medical imaging device 105, side camera 1015 can be pointed forward in an angle of 90 degrees with the lateral surface of the cylindrical shaped tube 1025, and front camera 1080 pointing forward to the front of the medical imaging device 1005. In some cases, the medical imaging device 1005 may be configured and designed to create an overlap between two fields view, in order to meet the requirement of certain medical procedures. Thus, in case a user utilizing the medical imaging device 1005 requires to change the field of view of the medical imaging device 1005, the medical imaging device may need to change with a new device which meets the specific medical procedure.

Figure 11:
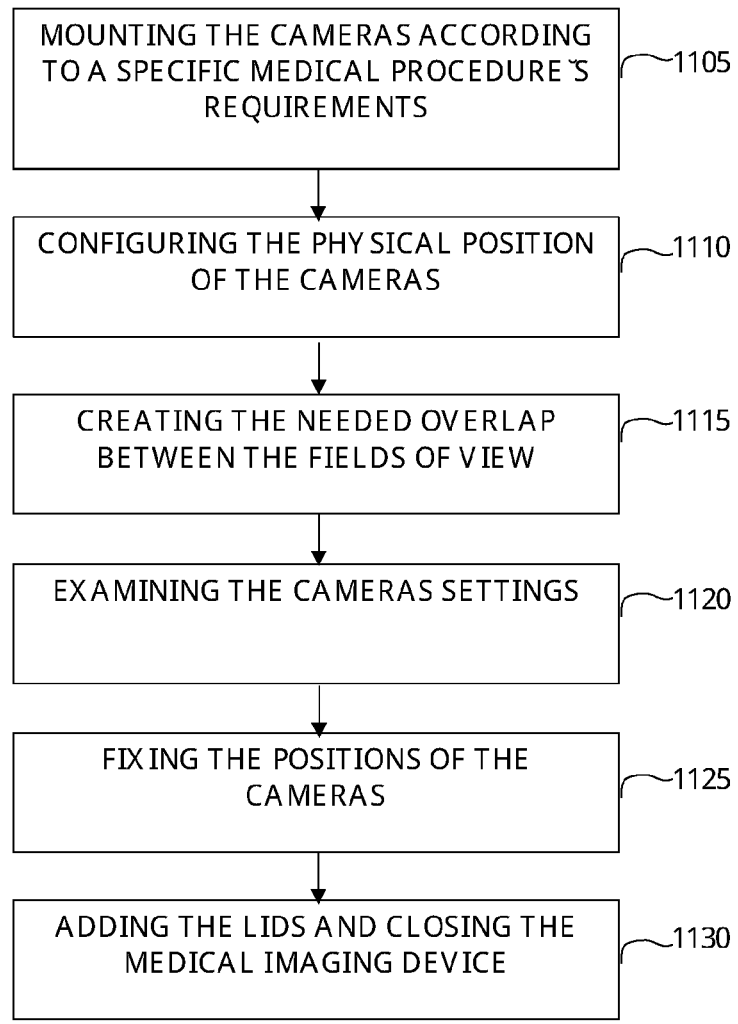
FIG. 11 discloses a method for producing a medical imaging device which meets specific requirements for septic medical procedure, according to exemplary embodiments of the present invention.

FIG. 11 discloses a method for producing a medical imaging device which meets specific requirements of a specific medical procedure, according to exemplary embodiments of the present invention. In step 1105, a user or a person who produce the medical imaging device may mount the cameras within a medical imaging device in accordance with specific medical procedure. The medical procedure may define the number of cameras required for such a medical procedure. For example, one specific medical procedure may require two cameras and another specific medical procedure may require three cameras. Step 1110 determines the configuration of the physical orientations of the cameras. The orientations may be defined as the specific point the camera may be located in the aperture of the medical imaging device, or the angle at which the camera is tilted. For example, a latera camera on the left may be located at the top section of the aperture and a right side camera may be required to be located down, close to the lower end of the side aperture of the cylindrical shaped tube.

In step 1115 the required overlap between the fields of view may be determined, in accordance with the specific medical procedure. The cameras located in their physical location may need to be tilted down, up, point aside, and the like. In some cases, the focal point of each camera may need to be adjusted in order to capture the required field of view. For example, a specific medical procedure may define a specific distance and direction between the cameras and the examined object, and the specific size of overlapping fields of view between the cameras. Thus, the user who produces the medical imaging device may position, move, adjust and configure the cameras according to the requirements of said specific medical procedure.

Step 1120 discloses examining the cameras settings and examining the filed view of the medical imaging device. Thus, the cameras mounted within the medical imaging device may need to be operated. A user or a tester which preforms the step may need to receive the captured field of view and define whether additional adjustments, are required, or not. The captured field of view may be in a format of a photo or a video displayed on a computerized device, a computer screen, an imaging device screen, and the like. In some cases, in which the field of view testing cannot meet the requirements of the medical procedure, the user who performs the testing is required to perform step 1105 again. In case step 1120 is complete, the tester performs step 1125 that discloses affixing the cameras to the right place. Such fixation may be with screws, bolts, soldering, brazing, laser welding, adhesive material, and the like. In some cases, once the affixing part has completed, the user who performs the testing may be required to conduct the step 1130. Step 1130 defines the closing part of the cylindrical shaped tube. Thus, a user may add the lids which support the functioning of the cameras and fix them. In some cases, a light filter may be added as well. Then, the user may close all parts of the cylindrical shaped tube and ensure the closing is hermetic. User may leak test the device following this step to assure seal integrity.

Figure 12:
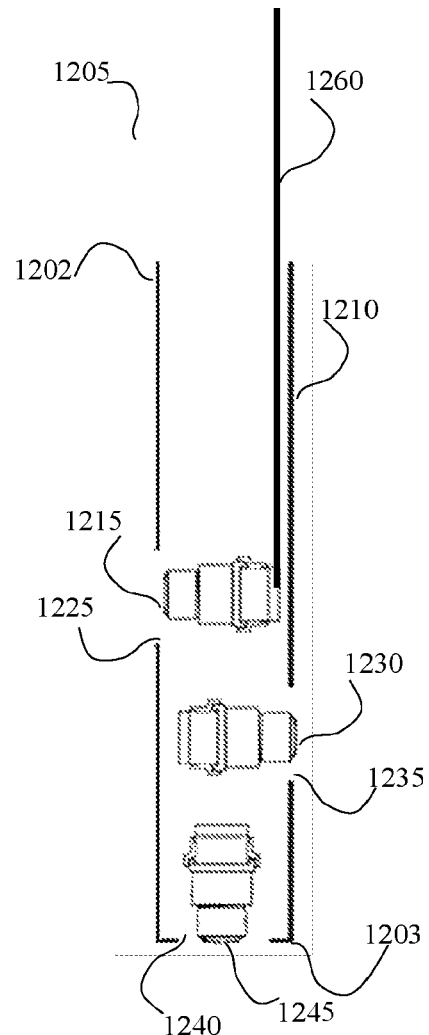
FIG. 12 shows a medical imaging device with three cameras in a vertical configuration, according to exemplary embodiments of the present invention.

FIG. 12 shows a medical imaging device with three cameras, according to exemplary embodiments of the present invention. FIG. 12 shows a cross-section of medical imaging device 1205. The medical imaging device 1205 comprises a cylindrical shaped tube 1210, comprises 3 cameras, camera 1215, 1230, and 1245, aligned one after the other between proximal side 1202 and distal end 1203 of the medical imaging device 1205. The distal end may be defined as the section in which the front camera 1245 is positioned.

Camera 1215 is pointed to the right side of the cylindrical shaped tube 1210, placed next to aperture 1225 and configured to be tilted up or down along the aperture 1225. Camera 1230 is pointed to the left side of the cylindrical shaped tube 1210, placed between camera 1215 and camera 1245, next to aperture 1235 and configured to be tilted up or down along the aperture 1235. Camera 1245 is pointed to the front side of the cylindrical shaped tube 1210, placed near camera 1230 and next to aperture 1240 and configured to be tilted right or left along the aperture 1240.

The medical imaging device 1205 also comprises adjusting rod 1260 designed to change the orientation of camera 1215. The adjusting rod 1260 is placed inside the cylindrical shaped tube 1210 to provide a user of the medical imaging device 1205 the ability to change the direction of camera 1215 along the aperture 1225. In some cases, the adjusting rod 1260 may be attached to camera 1230 in order to provide the user of the medical imaging device 1205 the ability to change the direction of camera 1230, in the same fashion as it is elaborated for camera 1215.

Figure 13:
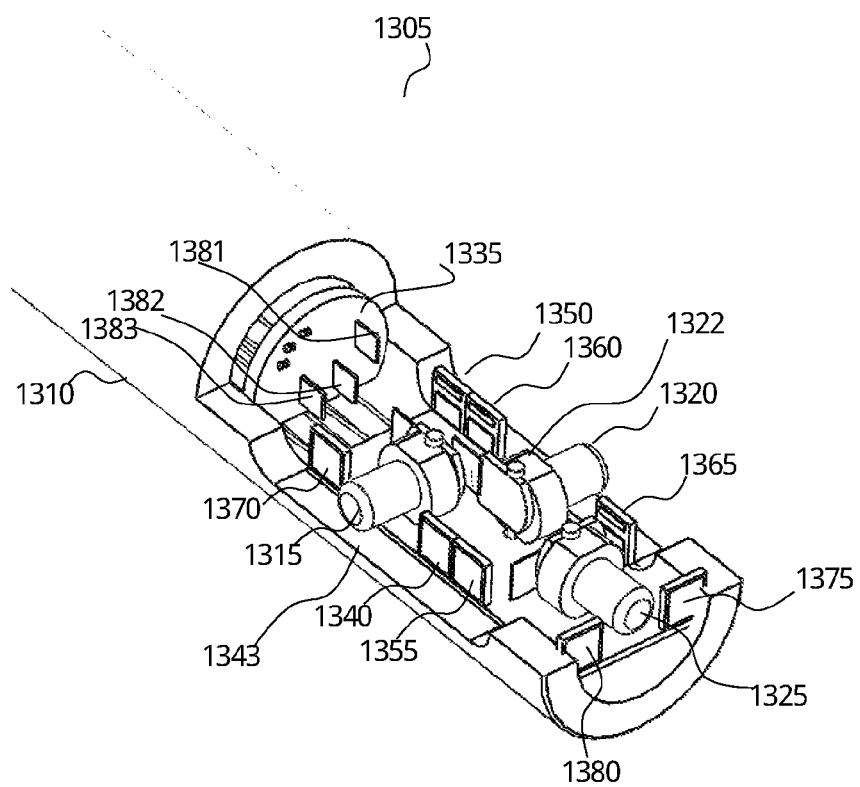
FIG. 13 shows a cross-section of a medical imaging device comprising 3 cameras and light sources, according to exemplary embodiments of the present invention.

FIG. 13 shows a cross-section of a medical imaging device comprising 3 cameras and light sources, according to exemplary embodiments of the present invention. Medical imaging device 1305 comprising a cylindrical shaped tube 1310, with 3 cameras 1315, 1320, and 1325. The cylindrical shaped tube 1310 comprises an aperture 1343 via which the camera 1315 can capture the vicinity of the medical imaging device 1305. The camera can tilt right and left along the aperture 1343. The cylindrical shaped tube 1310 also comprises light sources 1355, 1340, and 1370 placed in parallel to the aperture 1343 and designed to illuminate the field of view of camera 1315. Such light source may be a LED or other light sources desired by a person skilled in the art. Similarity, the cylindrical shaped tube 1310 comprises light sources 1350, 1360 and 1365 placed in parallel to aperture 1322 and designed to illuminate the field of view of camera 1320. Similarity, the cylindrical shaped tube 1310 comprises light sources 1380 and 1375, designed to illuminate the field of view of camera 1325, similar to the illumination provided by light sources 1355, 1340, and 1370.

Figure 14:
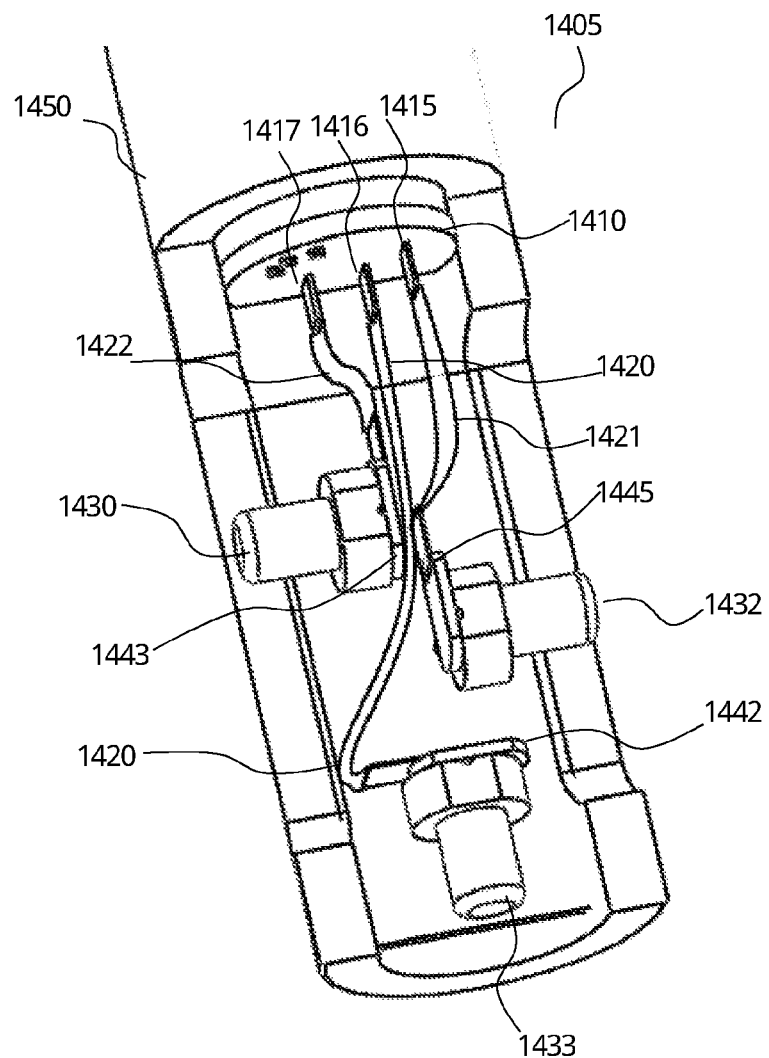
FIG. 14 shows a lateral view of a cross-section of a medical imaging device comprises 3 cameras attached with a printed circuit boards and light sources, according to exemplary embodiments of the present invention.

Medical imaging device 1305 also comprises a PCB 1335 (Printed Circuit Board), and connectors 1381, 1382, and 1383. PCB 1335, designed to deliver power to internal components of the medical imaging device 1305, via connectors 1381, 1382, and 1383. Such components may be the light sources, capacitors, resistors the cameras and other electrical components which may be located within the medical imaging device 1305. The PCB 1335 is configured to deliver power and receive data required for the functionality of the internal component of the medical imaging device 1305. The data required for the functionality may be digital or analog images from the cameras, digital or analog video files from the cameras, and the like. FIG. 14 shows a lateral view of a cross-section of a medical imaging device comprises 3 cameras attached with printed circuit boards, according to exemplary embodiments of the present invention. Medical imaging device 1405 comprising a cylindrical shaped tube 1450 equipped with a rigid PCB 1410 configured to provide electrical power to and receive data from the internal components of the medical imaging device 1405. Said received data from the internal components may be digital images from the cameras, digital video files from the cameras, and the like. The cylindrical shaped tube 1450 may also comprise elastic PCBs 1422, 1420, and 1421 designed and configured to transfer the data acquired from the cameras, 1432, 1433, and 1430 to the rigid PCB 1410. In some cases, the elastic PCB's 1422, 1420, and 1421 may be used to deliver electrical power to cameras 1432, 1433, and 1430.

The cylindrical shaped tube 1450 also comprises a PCB connector 1442 which connects the elastic PCB 1420 to camera 1433. In some cases, the elastic PCB 1420 may be pluggable. In some other cases, the elastic PCB 1422 may be static without the ability to be plugged off the PCB connector 1442. Similarity, PCB connector 1443 connects the elastic PCB 1422 to camera 1430 and PCB connector 1445 connects the elastic PCB 1421 to camera 1432.

In some cases PCB 1410, PCB 1422, 1420 and 1421 are manufactures as one single part of type Rigid—Flexible—Rigid.

Figure 15:
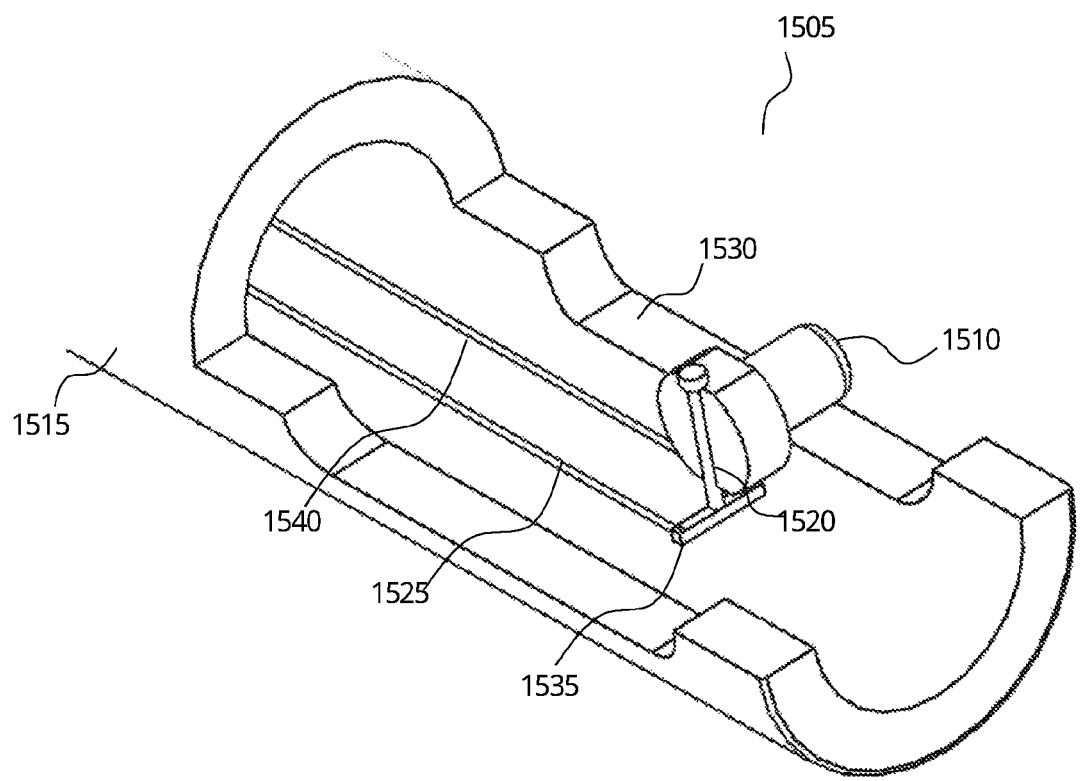
FIG. 15 shows a lateral view of a cross-section of a medical imaging device comprising one camera utilizing a pivot to rotate and change the direction view, according to exemplary embodiments of the present invention.

FIG. 15 shows a lateral view of a cross-section of a medical imaging device comprising one camera utilizing a pivot to rotate and change the direction view, according to exemplary embodiments of the present invention. FIG. 15 shows a medical imaging device 1505 comprising a cylindrical shaped tube 1515 as elaborated and disclosed above. The cylinder shaped tube 1515 comprises an aperture 1530 utilized to support the functionality of camera 1510 as disclosed above. The cylinder shaped tube 1515 also comprises a camera 1510 fastened to the cylindrical shaped tube 1515 by pivot 1520. Pivot 1520 may be designed to provide the rotation movement to the camera 1510. For example, camera 1510 can rotate toward the right side of the aperture 1530 and/or toward its left side, and thereby change the camera 1510 direction of view. Pivot 1520 is positioned perpendicularly to small rod 1535 used to support the rotation of pivot movement of pivot 1520. The cylinder shaped tube 1515 also comprises rods 1540 and 1525 connected to small rod 1535 for controlling the rotation movement of camera 1510. For example, in case a user pulls the rod 1525, the small rod 1535 may move clockwise, and thereby camera 1510 may also move clockwise. Thus, camera 1510 may move clockwise, toward the right end of aperture 1530 and the view direction may change accordingly.

In some cases, the maneuver mechanism of the MSID is controlled by a user. In such a case, the MSID comprises a control unit, for example a control panel or a mechanism that converts the user's voice into commands executed by the MSID, for example moving the camera units according to the user's vocal commands. In some other cases the control mechanism is a mechanical lever located outside the body. In some other cases, the maneuver mechanism of the MSID is controlled by a software algorithm that maneuvers the camera units according to properties such as a specific medical procedure. In such a case, the MSID comprises an input unit configured to receive such properties used by the software algorithm to maneuver the two or more camera units.

While the disclosure has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the disclosed subject matter not be limited to the particular embodiment disclosed as the best mode contemplated for carrying out this invention, but only by the claims that follow.

The invention claimed is:

1. A medical imaging device, comprising: a rigid housing; at least two camera units located within said rigid housing, capturing images of different directions of view; a maneuver mechanism configured to change the physical orientation of a camera of the at least two camera units.

2. The medical imaging device of claim 1, wherein the at least two camera units comprise a front camera unit and a lateral camera unit.

3. The medical imaging device of claim 2, wherein the maneuvering mechanism maneuvers the lateral camera unit to capture a field of view at least partially overlapping with a field of view captured by the front camera unit.

4. The medical imaging device of claim 1, wherein the at least two camera units comprise a front camera unit and two lateral camera units.

5. The medical imaging device of claim 4, wherein the maneuvering mechanism maneuvers the two lateral camera units, such that each of the two lateral camera units captures a field of view at least partially overlapping with a field of view captured by the front camera.

6. The medical imaging device of claim 1, wherein a camera unit of the at least two camera units is located in a camera compartment, located in a vicinity of an aperture in the rigid housing.

7. The medical imaging device of claim 6, further comprising two or more lids configured to cover the two or more openings.

8. The medical imaging device of claim 7, wherein the two or more lids are transparent.

9. The medical imaging device of claim 7, wherein the two or more lids comprise light filters.

10. The medical imaging device of claim 1, wherein the maneuver mechanism is connected to a hinge connected to a camera unit of the at least two camera units, wherein rotating the hinge results in changing the camera's direction of view.

11. The medical imaging device of claim 1, wherein the maneuver mechanism is connected to two or more hinges connected to two or more camera units, simultaneously rotating the two or more hinges, thereby simultaneously changing the two or more camera's direction of view.

12. The medical imaging device of claim 1, wherein the maneuver mechanism comprises a pulley controlled from outside the patient's body.

13. The medical imaging device of claim 1, wherein the maneuver mechanism comprises an adjusting rod sliding in the rigid housing.

14. The medical imaging device of claim 1, wherein the maneuver mechanism is controlled by a user, wherein the device further comprises a control unit.

15. The medical imaging device of claim 1, wherein the maneuver mechanism is controlled by a software algorithm, wherein the device comprises an input unit configured to receive properties used by the software algorithm to maneuver the two or more camera units.

16. The medical imaging device of claim 1, wherein the maneuver mechanism has a notification element to notify the user about the camera's direction of view.

17. The medical imaging device of claim 1, wherein the rigid housing is made of a single rigid sheet of material.

18. The medical imaging device of claim 1, wherein said maneuver mechanism is physically connected to the at least two camera units.

* * * * *